United States Patent [19]

Rosenbaum

[11] Patent Number: 4,643,727
[45] Date of Patent: Feb. 17, 1987

[54] ABSORBANT PAD

[76] Inventor: Richard J. Rosenbaum, 3246 E. Easter Place, Littleton, Colo. 80122

[21] Appl. No.: 689,481

[22] Filed: Jan. 7, 1985

[51] Int. Cl.⁴ .............................................. A61F 13/00
[52] U.S. Cl. .................................... 604/369; 604/378
[58] Field of Search ............... 604/374, 369, 385, 387, 604/365, 378, 384, 366

[56] References Cited

U.S. PATENT DOCUMENTS

| | | | |
|---|---|---|---|
| 3,468,311 | 9/1969 | Gallagher | 604/370 |
| 3,559,649 | 2/1971 | Grad | 604/382 |
| 3,812,001 | 5/1974 | Ryan | 604/385 R |
| 3,881,491 | 5/1975 | Whyte | 604/385 R |
| 4,055,180 | 10/1977 | Karami | 604/374 |

*Primary Examiner*—Dalton L. Truluck
*Assistant Examiner*—Karen F. Kaechele
*Attorney, Agent, or Firm*—Max L. Wymore

[57] ABSTRACT

An absorbant pad having an intermediate plastic bubble layer covered on either side with a continuous layer of absorbant material wherein the bubble layer serves as a reservoir for a liquid that is siphoned around the edges of the bubble layer for storage.

4 Claims, 4 Drawing Figures

ABSORBANT PAD

BACKGROUND OF THE INVENTION

The present invention is directed to an improved absorbant pad, which may be used as a diaper, having particular utility in hospitals, nursing homes and the like.

It is a principal object of the present invention to provide an improved absorbant pad or diaper which comprises a plurality of layers which function together to accommodate large amounts of fluid therein.

A further object of the present invention is to provide such an absorbant diaper including a cushion layer, which comprises a plurality of air cells that are separate from each other and the other layers, to channel liquid flow in the most efficient routing.

A further object of the present invention is to provide a wicking layer on top of the air cell layer that extends over the edges of the air cell layer to direct and improve the liquid flow from the upper surface of the air cell layer to other absorbant layers lying below the air cell layer.

A further object of the present invention is to provide a diaper structure wherein the wicking layer is wrapped completely around the air cell layer.

A still further object of the invention is to provide a diaper structure wherein a liquid impervious layer is attached to or formed on the lower surface of the highly absorbant layer to prevent passage of fluids from the absorbant layer to a supporting structure.

A still further object of the present invention is to provide such an absorbant diaper that is relatively inexpensive to manufacture and which is disposable avoiding the necessity of laundering.

These and other objects and advantages are provided by a diaper comprising a plurality of layers and including at least a pneumatic cell layer, an absorbant wicking layer covering the top of the cell layer and wrapped around at least a pair of edges of the cell layer, a liquid absorbant layer and a bottom liquid impervious layer. The diaper also contemplates a structure where the absorbant wicking layer is wrapped entirely around the cell layer to provide maximum wicking action of the fluid from the cell layer to the absorbant layer below the cell layer.

Other inventors have tried to solve these problems without complete success, such as U.S. Pat. No. 3,468,311, which is directed to an absorbant pad having an air bubble layer in which are provided a plurality of liquid permeable perforations to provide a passageway for fluids therethrough to a lower highly absorbant layer; however, the structure does not provide even flow of the fluid therethrough.

The patented absorbant pad comprises a pneumatic cellular cushion top layer, a liquid absorbant layer and a bottom liquid impervious layer. The upper most layer comprises a pneumatic cellular cushion layer and the bottom layer comprises a liquid impervious plastic sheet with a highly absorbant layer in between the cushion layer and the impervious plastic layer. The top-most layer comprises a pair of plastic sheets assembled to provide a plurality of air or other fluid filled cells which cells are spaced from each other by partition zones formed by sealing opposed surfaces of the sheets together. Between the cells and in the partition walls are a plurality of perforations large enough to permit generally unrestricted liquid flow from the cushion layer to the absorbant layer.

U.S. Pat. No. 4,360,015 is directed to a multilayer absorbant structure having two absorbant layers separated by a grid material and covered on one side by an exterior layer which contacts a wound surface and on the other side by a moisture resistant barrier. The outer wound contacting layer adjacent the absorbant layer may be unwoven. The next grid layer is non-absorbant but has openings through the grid through which fluids to be absorbed passes. The next layer is absorbant material while the exterior layer is a fluid barrier.

Other prior art patents that are of possible interest are: U.S. Pat. Nos. 2,896,618, 3,886,941, 3,889,679, 4,055,180, 4,321,924, 4,323,609, 4,338,371, 4,381,783, 4,411,660.

For a better understanding of the present invention, together with other and further objects thereof reference is had to the following description taken with the drawings and its scope will be pointed out in the appended claims.

Figure 1:
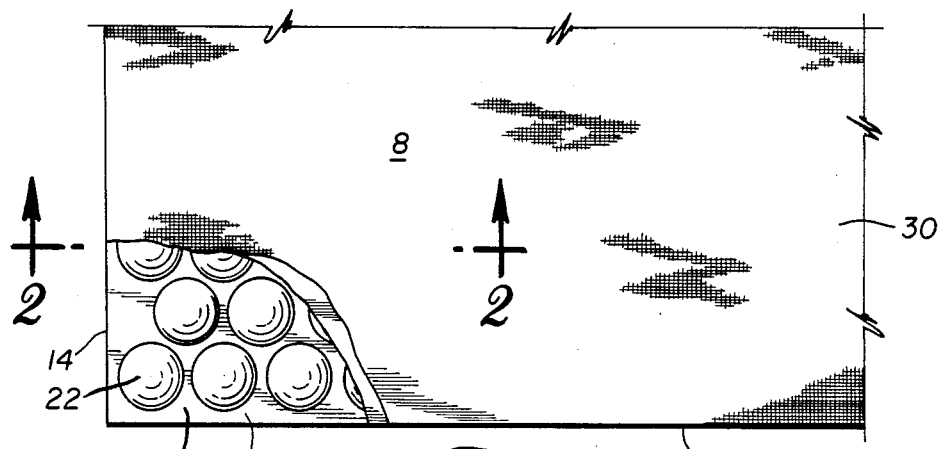
FIG. 1 is a top plan view of a diaper constructed in accordance with the teachings of the present invention with portions broken away.
Figure 2:
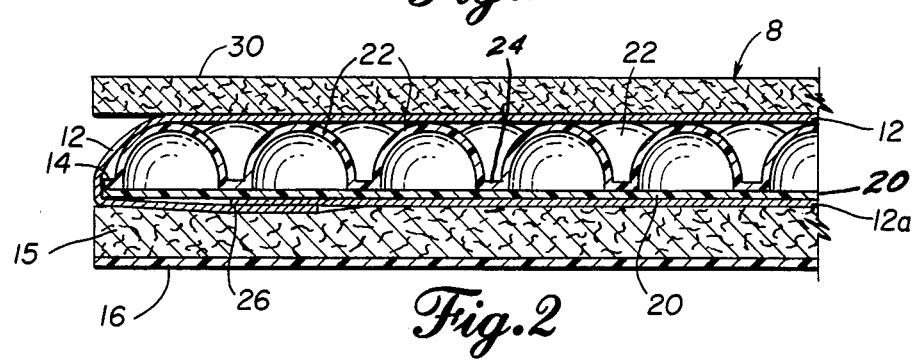
FIG. 2 is a view along line 2—2 of FIG. 1.
Figure 3:
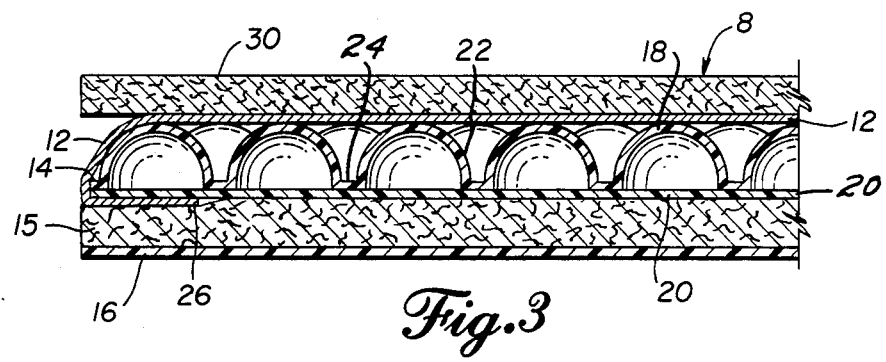
FIG. 3 is a cross sectional view of another form of the present invention.

Referring to the drawings, the improved diaper 8 is comprised of at least four layers. The uppermost layer generally designated as 10 comprises an air cell cushion layer; 12 represents a highly absorbant wicking layer that completely covers the top of the air cells of the air cell layer and is wrapped around at least an opposing pair of sides 14 of the air cell layer. Immediately beneath the folded under portions of the wicking layer 12 is an absorbant layer 15 of wadding and the like and the bottom layer 16 is a liquid impervious plastic layer.

The uppermost layer 10 comprises a pair of liquid impervious plastic sheets 18 and 20 sealed together to form a plurality of air bubbles or cushions 22. The air bubbles are separated from each other by sealed zones 24 formed by sealing opposed portions of the sheets 18 and 20 together. Preferably the air bubbles 22 are uniformly spread about the top layer and provide a highly desirable cushion effect. The air bubbles 22 are located and present in such numbers that the uncontrolled flow of liquid onto the top layer is divided and spaced evenly over the top layer so that the liquid will not overflow the edges of that layer.

The wicking layer 12 is positioned on top of the air bubble layer 10 and is folded over at least one pair of edges or sides 14 and preferably all sides 14 of the air bubble layer 10. The folded over portion 26 of the layer 12 may extend inwardly only a short distance but preferably will cover all of the lower surface of the air bubble layer 10 as well.

The wicking layer 12 may be of paper toweling and the like in which a liquid will migrate very rapidly to the marginal edges of the air bubble layer 10 and over the edges 14 to a lower absorbant layer.

The absorbant layer 15 may comprise substantially any of the highly absorbant material or synthetic fibers, woven, non-woven or porous materials. Good results have been obtained by the use of mats or batts of synthetic fibers, mixtures of synthetic fiber, non-woven cellulosic batts or open cell sponge-like sheets. In a specific embodiment of the present invention the absorbant layer 15 comprised cotton wadding.

The absorbant layer 15 may comprise a mat or mass of hydrophobic fibers wherein the liquid retaining function of the batt takes place along the large surface area of the fibers. Non-water wetting fibers such as Dacron and Nylon have the characteristic property of being non-water absorbant from the standpoint that water generally does not penetrate the fibers; however, such fibers have the characteristic of permitting fluids to wick along their surface and in the manner a batt of such fibrous material will retain or hold a large quantity of liquid on its large surface area when disposed in batt arrangement.

The bottom layer 16 of the diaper preferably is comprised of a thin layer of water impervious plastic such as polyethylene, polypropylene and the like. The primary function of the layer 16 is to provide a barrier for liquids contained in the layer 15.

The uppermost layer 10 preferably comprises a liquid impervious plastic sheet provided with a plurality of air bubbles.

Figure 4:
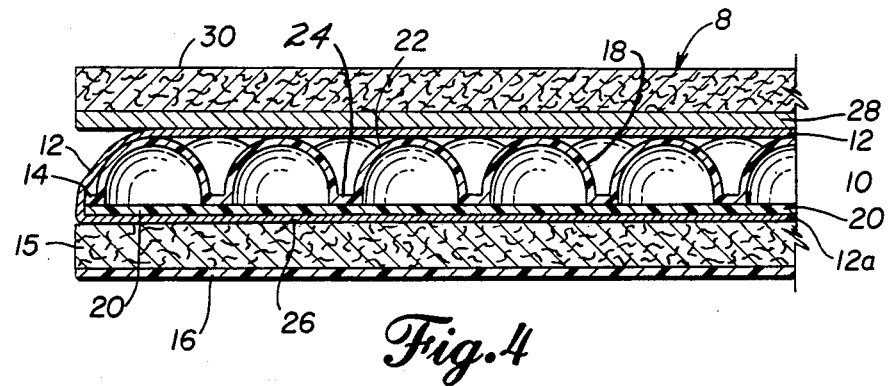
FIG. 4 is a cross sectional view of still another form of the present invention.

As best seen in FIG. 4, the preferred embodiment of the present invention comprises an uppermost layer 28 of Pellon. The next layer 30 is cellulose tissue. The wicking layer 12 is of paper toweling which completely surrounds the air bubble layer 10 having a cushion function. The absorbant layer 15 is of cotton wadding and the bottom layer 16 is of plastic.

In use, the embodiment shown in FIG. 4 receives liquids via the cellulose tissue layer 30 which transfers the excess liquid to a Pellon layer 28. The excess liquid from layer 30 is delivered to the Pellon layer 28 and then to the upper paper towel wicking layer 12 which wicks some of the liquid around the edges 14 of the air bubble layer 10 while the bulk of the liquid is delivered by the upper wicking layer 12 to the air bubble layer 10. The air bubbles 22 projecting upwardly present a barrier pattern to the incoming liquid and breaks the liquid stream into a multitude of small streams or riverlets which migrate to the edges 14 and discharge into the lower wicking layer 12a for even discharge across the surface of the absorbant layer 15. The bottom layer 16 prevents liquids from escaping the absorbant layer.

With the foregoing description, it is seen that the present invention has accomplished the objectives desired with a non-complicated inexpensive structure with superior control of liquids within an absorbant diaper.

While there have been described what at present are considered to be the preferred embodiments of this invention, it will be obvious to those skilled in the art that various changes and modifications may be made therein without departing from the invention. It is aimed, therefore, in the appended claims to cover all such changes and modifications which fall within the true spirit and scope of the invention.

What is claimed is:

1. An absorbant diaper construction comprising:
a plurality of layers and including at least a pneumatic liquid impervious cellular layer having a top with cells, a bottom and edge;
a wicking layer positioned at least above the top of the cellular layer and having portions wrapped around the edges thereof positioned adjacent the bottom of the cellular layer;
a bottom liquid impervious layer coextensive with said cellular layer; and,
a liquid absorbant layer between said cellular layer and said bottom layer thereof with said pneumatic cellular layer comprising a pair of plastic sheets having a plurality of air cells formed therebetween with unobstructed fluid directing passageways between the air cells, with the cells almost entirely formed in the top plastic sheet and said cellular layer forming a liquid tight barrier against a liquid passing therethrough.

2. A diaper according to claim 1 wherein the wicking layer completely surrounds the cellular layer including the top, sides and bottom thereof.

3. A diaper comprising:
a plurality of layers and having a pneumatic cellular layer formed of upper and lower sheets of plastic with edges and connected to have a plurality of air cells formed in the upper sheet with unobstructed fluid directing passageways between the air cells;
a wicking layer covering the upper sheet and the air cells formed therein with the wicking layer being wrapped around both the edges completely surrounding the upper and lower sheets of plastic forming the top and bottom of the cellular layer, said upper plastic sheet of the cellular layer forming a liquid impervious barrier to the passage of liquid and a liquid absorbant layer having a liquid impervious bottom layer coextensive with said cellular layer positioned between the wicking layer and said bottom layer.

4. An absorbant diaper construction comprising:
a plurality of layers with the top layer having a liquid impervious upper layer connected with a lower layer to form air cells therewith, with unobstructed fluid directing passageways between the air cells, a bottom and edge;
a wicking layer positioned at least above the air cells of the liquid impervious upper layer with portions of the wicking layer wrapped around the edges thereof positioned adjacent the bottom of the lower layer; and,
a bottom liquid impervious layer with a liquid absorbant layer positioned in between and coextensive with the air cell top layer and the lowermost bottom wherein the wicking layer substantially completely surrounds the liquid impervious upper layer including the top, edge and bottom thereof.

* * * * *